(12) United States Patent
Zoellkau et al.

(10) Patent No.: US 10,258,044 B2
(45) Date of Patent: Apr. 16, 2019

(54) TERNARY HERBICIDE COMBINATIONS

(71) Applicant: BAYER CROPSCIENCE AKTIENGESELLSCHAFT, Monheim am Rhein (DE)

(72) Inventors: Achim Zoellkau, Cologne (DE); Dominique Schreiber, Anche (FR)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 14/910,516

(22) PCT Filed: Aug. 5, 2014

(86) PCT No.: PCT/EP2014/066777
§ 371 (c)(1),
(2) Date: Feb. 5, 2016

(87) PCT Pub. No.: WO2015/018812
PCT Pub. Date: Feb. 12, 2015

(65) Prior Publication Data
US 2016/0174560 A1    Jun. 23, 2016

(30) Foreign Application Priority Data
Aug. 9, 2013    (EP) .................................... 13179813

(51) Int. Cl.
| A01N 47/36 | (2006.01) |
| A01N 47/38 | (2006.01) |
| A01N 43/90 | (2006.01) |
| A01N 43/40 | (2006.01) |
| A01N 43/80 | (2006.01) |

(52) U.S. Cl.
CPC ............ *A01N 47/36* (2013.01); *A01N 43/40* (2013.01); *A01N 43/90* (2013.01); *A01N 47/38* (2013.01)

(58) Field of Classification Search
CPC combination set(s) only.
See application file for complete search history.

(56) References Cited

U.S. PATENT DOCUMENTS

| 4,902,340 A | 2/1990 | Hubele | |
| 5,688,745 A * | 11/1997 | Ort | A01N 47/36 504/231 |
| 6,221,809 B1 * | 4/2001 | Hacker | A01N 47/36 504/136 |
| 6,251,827 B1 | 6/2001 | Ziemer et al. | |
| 6,492,301 B1 | 12/2002 | Hacker et al. | |
| 6,864,217 B2 | 3/2005 | Hacker et al. | |
| 6,914,035 B2 | 7/2005 | Ziemer et al. | |
| 7,781,374 B2 * | 8/2010 | Feucht | A01N 47/38 504/139 |
| 7,858,805 B2 | 12/2010 | Gesing et al. | |
| 7,915,199 B1 * | 3/2011 | Glock | A01N 43/90 504/105 |
| 8,404,618 B2 | 3/2013 | Plant et al. | |
| 8,551,918 B2 | 10/2013 | Polge | |
| 2005/0026784 A1 | 2/2005 | Hacker et al. | |

(Continued)

FOREIGN PATENT DOCUMENTS

| AU | 2002/356585 B2 | 9/2007 |
| CH | 2004/000767 | 4/2004 |

(Continued)

OTHER PUBLICATIONS

Rummens, F.H.A., "An improved definition of synergistic and antagonistic effects," Weed Science, vol. 23(1), pp. 4-6 (1975).*

(Continued)

*Primary Examiner* — John Pak
(74) *Attorney, Agent, or Firm* — McBee Moore Woodward & Vanik IP, LLC

(57) ABSTRACT

Herbicide combinations comprising an effective amount of components (A), (B) and (C) wherein
(A) denotes one or more herbicides selected from the group of compounds of the formula (I) and salts thereof

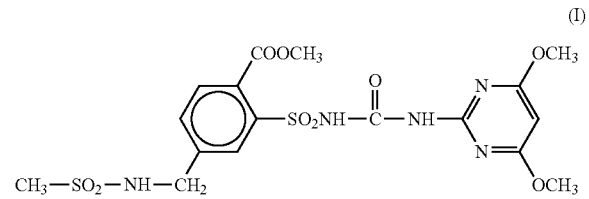

(B) denotes one or more herbicides selected from the group of the compounds of the formula (II) and their salts

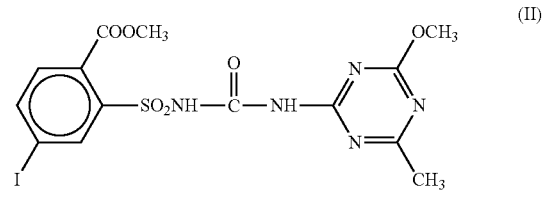

(C) denotes at least one compound selected from the group consisting of
(C-1) thienecarbazone-methyl;
(C-2) pyroxsulam;
(C-3) halauxifen;
(C-4) pinoxaden;
(C-5) pyroxasulfone;
and/or salts thereof.

18 Claims, No Drawings

(56) References Cited

U.S. PATENT DOCUMENTS

| | | | |
|---|---|---|---|
| 2005/0070437 A1 | 3/2005 | Hacker et al. | |
| 2006/0154823 A1* | 7/2006 | Witschel | A01N 43/90 504/136 |
| 2006/0205599 A1 | 9/2006 | Hacker et al. | |
| 2013/0190179 A1 | 7/2013 | Hain et al. | |
| 2015/0175543 A1* | 6/2015 | Satchivi | A01N 43/40 504/105 |

FOREIGN PATENT DOCUMENTS

| | | |
|---|---|---|
| DE | 196 50 955 | 6/1998 |
| WO | 9213845 A1 | 8/1992 |
| WO | 9510507 A1 | 4/1995 |
| WO | 98/47356 A2 | 10/1998 |
| WO | 0105788 A1 | 1/2001 |
| WO | 02/060255 A2 | 8/2002 |
| WO | 03/022050 A1 | 3/2003 |
| WO | 03/043422 A1 | 5/2003 |
| WO | 03/073854 A1 | 9/2003 |
| WO | 2004/014138 A1 | 2/2004 |
| WO | 2004/080171 | 9/2004 |
| WO | 2005/009133 A1 | 2/2005 |
| WO | 2005/011383 A1 | 2/2005 |
| WO | 2005/055716 A2 | 6/2005 |
| WO | 2005/104848 A1 | 11/2005 |
| WO | 2009/025918 A2 | 3/2009 |
| WO | 2011107741 | 9/2011 |
| WO | 2012/049266 A1 | 4/2012 |
| WO | 2013034513 A2 | 3/2013 |

OTHER PUBLICATIONS

Richer, D.L., "Synergism—a patent view," Pesticide Science, vol. 19, pp. 309-315 (1987).*
Colby, S.R., "Calculating synergistic and antagonistic responses of herbicide combinations," Weeds, vol. 15, pp. 20-22 (1967).*
Database WPI Week 201268 XP002716877.
International Search Report of PCT/EP2014/066777 dated Oct. 6, 2014.
Owen "Herbicidal Compositions", Declaration of Dr. Michael D.K. Owen, (Mar. 26, 2013), p. 1-71.
Owen "Professor and Weed Science Extension Specialist", Resume, p. 1-118.
Polge "Herbicidal Compositions", U.S. Appl. No. 60/527061, filed Dec. 4, 2003, p. 1-22.
Owen et al. "Evaluation of preemergence applications of KIH-485, s-metolachlor & CGA-154281, and s-metolachlor & atrazine & CGA-154281 for crop phytotoxicity and weed control in corn, Nashua, IA, 2003," (2003), NCWSS Research Report, vol. 60, pp. 51-52 (2003).
Joanna Davies "Herbicide Safeners—Commercial Products and Tools for Agrochemical Research", Pesticide Outlook, The Royal Society of Chemistry, (Feb. 2001) pp. 10-15.
Fedtke et al. "Synergistic Activity of the Herbicide Safener Dichlormid with Herbicides Affecting Photosynthesis", Zeitschrift für Naturforschung, Section C, Biosciences 1990 vol. 45 No. 5 pp. 565-556.
Sprague et al. "Enhancing the Margin of Selectivity of RPA 201772 in Zea mays with Antidotes", Weed Science, vol. 47, No. 5, pp. 492-497 (Sep.-Oct. 1999).
Leuschen et al. "Effects of a Seed-Applied Safener on Corn Injury From Clomazone, Imazaquin and Imazethapyr", University of Minnesota Southern Experiment Station Research Report, pp. 72-73 (1989).
Pyroxasulfone (KIH-485) chemical structure, Wildlife International, Ltd., pp. 1-7.
"Corn Injury from Balance Herbicide", University of Illinois Extension Publication (May 28, 1999), pp. 1-5.
"Herbicide Manual for Agricultural Professionals", Iowa State University Manual for Agricultural Professionals (2004).
Friesen et al. "The Influence of Temperature and Soil Moisture on the Phytotoxicity of Dicamba, Picloram, Bromoxynil, and 2,4-D Ester", Can. J. Plant Sci. (1966); vol. 46: pp. 653-660.
"Herbicide Injury Symptoms on Corn and Soybean", Purdue Extension Publication, printed (Apr. 13, 2017), pp. 1-17.
David W. Cudney "Why Herbicides are Selective", California Exotic Pest Plant Council (1996) Symposium Proceedings, pp. 1-3.
J.D. Burton et al. "Sulfonylurea Selectivity and Safener Activity in Landmark and 'Merit' Sweet Corn", Pesticide Biochem. and Physiol. (1994); vol. 48(3): pp. 163-172.
Maxwell et al. "Crop response from corn herbicides on two sweet corn varieties". Urbana, Illinois, (2004). NCWSS Research Report, vol. 61, pp. 8-10.
Gunsolus et al. "Herbicide Mode of Action and Injury Symptoms", North Central Regional Publication 377: (2002) pp. 1-19.
O'Sullivan et al. "Sweet corn (Zea mays) cultivar tolerance to primisulfuron", Can. J. Plant Sci. (2001); pp. 261-264.
Hwang et al. "Mode of Safening Action of Naphthalic Anhydride Against Injury of Sulfonylurea and Imidazolinone Herbicides in Maize", Council of the Australasian Weed Soc. Inc., 10th Australian Weeds Conference/14th Asian-Pacific Weed Science Society Conference 1993.
Rowe et al. I., Efficacy and Mode of Action of CGA-154281, A Protectant for Corn (Lea mays) from Metolachlor Injury. Weed Science. 1991; 39:78-82.
Zidua Herbicide Label from BASF.
Ritter et al., First Year Experiences with KIH-485. NEWSS 58:18 (2004) http://www.newss.org/proceedings/proceedings_2004_vol58.pdf., pp. 1-5.
Zollinger et al. "Crop Response to KIH-485 carryover". NCWSS Research Report, vol. 61, pp. 34-35 (2004).
Mallory-Smith et al. "Revised Classification of Herbicides by Site of Action for Weed Resistance Management Strategies", Weed Technology. (2003); vol. 17: pp. 605-619.
Wicks et al. "Isoxaflutole (Balance) Herbicide Injury to Corn in Nebraska", pp. 1-8.
Dewell et al. "Preemergence weed control in corn with s-metolachlor &atrazine&mesotrione and s-metolachlor&mesotrion premixes. Wanatah, IN, 2003", (2003), NCWSS Research Report, vol. 60, pp. 70-71.
Nelson et al. "Safening of Isoxaflutole in Corn", NCWSS Research Report, vol. 56, p. 76 (2001).
Steckel et al. "Soil Factor Effects on Isoxaflutole Plus Flufenacet Phytotoxicity in Two Corn Hybrids". NCWSS Research Report, vol. 56, p. 145 (2001).
Kelley et al. "Soybean Response to Plant Growth Regulatory Herbicides", NCWSS Research Report, vol. 56, p. 100 (2001).
Ditmarsen et al. "Crop Tolerance and Efficacy of Flumetsulam + Clopyralid Tank Mixed with Reduced Rates of Dicamba + Diflufenzopyr in Field Corn", NCWSS Research Report, vol. 56, p. 218 (2001).
Wyk et al. "Maize Cultivars Differ in Tolerance to Imazethapyr", South African Journal of Plant and Soil (2000); 17:2, p. 86-89.
Curran et al. "Herbicide Injury-Photosynthetic Inhibitors and Contact Herbicides", University of Illinois Extension.
Phatak et al. "Chapter 13: Growth Regulators, Fungicides and other Agrochemicals as Herbicide Safeners", Crop Safeners for Herbicides (1989) pp. 299-315.
Owen et al. "Evaluation of Crop Phytotoxicity and Weed Control in Corn with Postemergence Applied Nicosulfuron & Rimsulfuron, Atrazine, Mesotrione and others, Ames, IA, 2002," (2002), NCWSS Research Report, vol. 59, p. 108-109.
Trower "Sweet Corn Tolerance to Postemergence Applications of Formasulfuron" (2003) NCWSS Research Report, vol. 60, pp. 16-17.
Johnson et al. "Nicosulfuron, Primisulfuron, Imazethapyr and DPX-PE350 Injury to Succeeding Crops" (1993), Weed Tech.; vol. 7(3): 641-644.
Striegel et al. "Formasulfuron + Isoxadifen—Success and Lessons Learned from a Launch Year", North Central Weed Science Proceedings, vol. 57: 225 (2002).
DuPont Web Printout explaining "Q" herbicides, "Safened Sulfonylurea Herbicides Reduce Risk of Corn Injury", Pioneer, printed (Apr. 14, 2007) pp. 1-6.

(56) References Cited

OTHER PUBLICATIONS

Schultz et al. "A Comparison of Safeners for Metolachlor on Corn", North Central Weed Science Proceedings, vol. 59:11 (2004), pp. 1-2.
Rowe et al. "Factors Affecting Chloroacetanilide Injury to Corn" (*Zea mays*). Weed Technology. 1990; 4(4): 904-906.
"Postemergence Control of Grass Weeds in field Corn" Purdue Weed Science, Publication (May 21, 2003), pp. 1-1.
David Hest "Mixing It Up", Farm Industry News (Jan. 1, 2003), pp. 1-10.
Hartzler et al. "2005 Iowa State University Manual for Agricultural Professionals" (1996-2006) pp. 1-115.
"Isoxaflutole" chemical structure, Phenomenex Applications; printed (Apr. 26, 2017). pp. 1-2.

* cited by examiner

TERNARY HERBICIDE COMBINATIONS

CROSS REFERENCE TO RELATED APPLICATIONS

This application is a § 371 National State Application of PCT/EP2014/066777, filed Aug. 5, 2014, which claims priority to European Application No. 13179813.4 filed Aug. 9, 2013.

BACKGROUND OF THE INVENTION

Field of the Invention

The invention is in the technical field of crop protection products which can be employed against harmful plants, for example in crop plants, and which comprise, as active compounds, a combination of at least three herbicides.

Description of Related Art

The documents WO 92/13845 and WO 95/10507 disclose sulfonylureas and their salts and also their use as herbicides and/or plant growth regulators.

WO 03/073854 discloses ternary combinations containing the sulfonylurea herbicides iodosulfuron and mesosulfuron and further herbicides, such as procarbazone.

WO 2004/080171 A2 discloses synergistic herbicidal mixtures comprising A) pyroxsulam or its salts, B) at least one herbicidal compound selected from a long list of further herbicides, and, if desired, C) at least one safener.

U.S. Pat. No. 6,221,809 B1 discloses binary combinations comprising (i) mesosulfuron or a salt thereof, and (ii) a further herbicide, among which iodosulfuron is mentioned.

U.S. Pat. No. 6,492,301 B1 and U.S. Pat. No. 6,864,217 B1 disclose herbicidal compositions containing (i) at least one herbicidally active compound from the group of certain substituted phenylsulfonylureas and their agriculturally acceptable salts, and (ii) at least one compound from the group of herbicides which are selective in rice.

WO 2009/029518 A2 discloses combinations containing (i) a pyridine or pyrimidine carboxylic acid component, such as for example halauxifen, and (ii) a second cereal or rice herbicide component, wherein inter alia sulfonylurea herbicides such as iodosulfuron and mesosulfuron are mentioned.

WO 2011/107741 A1 discloses herbicidal compositions comprising a mixture of (a) a first herbicide of a certain type and (b) pinoxaden.

Substituted thien-3-ylsulfonylamino(thio)carbonyltriazolin(ethi)ones are known to be effective herbicides (cf. WO 01/05788).

The efficacy of these herbicides against harmful plants in the crop plants is at a high level, but depends in general on the application rate, the formulation in question, the harmful plants or spectrum of harmful plants to be controlled in each case, the climatic conditions, the soil conditions and the like. Another criterion is the duration of action, or the breakdown rate of the herbicide. If appropriate, changes in the sensitivity of harmful plants, which may occur upon prolonged use of the herbicides or within geographic limitations must also be taken into consideration. The compensation of losses in action in the case of individual harmful plants by increasing the application rates of the herbicides is only possible to a certain degree, for example because such a procedure frequently reduces the selectivity of the herbicides or because the action is not improved, even when applying higher rates. In some cases, the selectivity in crops can be improved by adding safeners. In general, however, there remains a need for methods to achieve the herbicidal action with a lower application rate of active compounds. Not only does a lower application rate reduce the amount of an active compound required for application, but, as a rule, it also reduces the amount of formulation auxiliaries required. It both reduces the economic input and improves the ecological compatibility of the herbicide treatment.

One possibility of improving the application profile of a herbicide can consist in combining the active compound with one or more other active compounds. However, the combined use of a plurality of active compounds frequently causes phenomena of physical and biological incompatibility, for example a lack of stability in a coformulation, decomposition of an active compound, or antagonism of the active compounds. What is desired are, in contrast, combinations of active compounds having an advantageous activity profile, high stability and, if possible, a synergistically improved action, which allows the application rate to be reduced in comparison with the individual application of the active compounds to be combined.

Surprisingly, it has now been found that certain active compounds from the group of sulfonylureas or their salts in combination with certain herbicides, preferably ALS inhibiting herbicides from the group of the sulfonylamino-carbonyltriazolinones, in particular, thiencarbazone (C)

act together in a particularly advantageous manner, for example when they are employed in crop plants which are suitable for the selective use of the herbicides, if appropriate with addition of safeners.

SUMMARY

The invention therefore provides herbicide combinations comprising an effective amount of components (A), (B) and (C), wherein (A) denotes one or more herbicides selected from the group of the compounds of the formula (I) and their salts

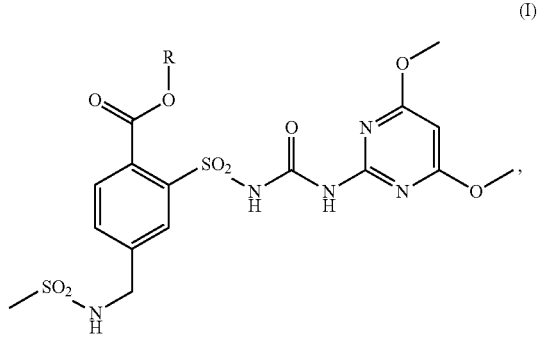

wherein R is hydrogen or a $C_1$-$C_5$-alkyl group, preferably R is methyl;

(B) denotes one or more herbicides selected from the group of the compounds of the formula (II) and their salts

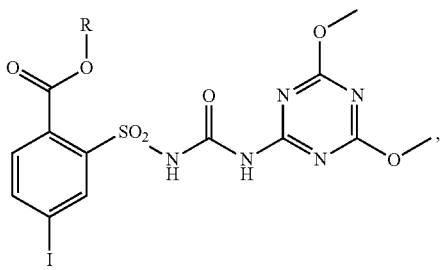

(II)

wherein R is hydrogen or a $C_1$-$C_5$-alkyl group, preferably R is methyl;

(C) denotes at least one compound selected from the group consisting of
(C-1) thienecarbazone-methyl;
(C-2) pyroxsulam;
(C-3) halauxifen;
(C-4) pinoxaden;
(C-5) pyroxasulfone;
and/or salts or esters thereof.

DETAILED DESCRIPTION OF A PREFERRED EMBODIMENT

If, in the context of this description, the short form of the common name of an active compound is used, this includes in each case all customary derivatives, such as the esters and salts, and isomers, in particular optical isomers, in particular the commercially available form or forms. If the common name denotes an ester or salt, this in each case also comprises all other customary derivatives, such as other esters and salts, the free acids and neutral compounds, and isomers, in particular optical isomers, in particular the commercially available form or forms. The given chemical compound names denote at least one of the compounds embraced by the common name, frequently a preferred compound. In the case of sulfonamides such as sulfonylureas, salts also include the salts formed by exchanging a hydrogen atom on the sulfonamide group by a cation.

The herbicide (C) is suitable for controlling monocotyledonous and dicotyledonous harmful plants.

The salts of compounds of the formulae (I) and (II) in the context of the present invention preferably are in the form of the respective alkali metal salts, alkaline earth salts or ammonium salts, preferably in the form of the respective alkali metal salts, more preferably in the form of the respective sodium or potassium salts, most preferably in the form of the respective sodium salts.

The salts of compounds (C) in the context of the present invention preferably are in the form of the respective alkali metal salts, alkaline earth salts or ammonium salts, preferably in the form of the respective alkali metal salts, more preferably in the form of the respective sodium or potassium salts, most preferably in the form of the respective sodium salts.

The herbicide combinations according to the invention comprise a herbicidally effective amount of components (A), (B) and (C) and may comprise further components, for example agrochemically active compounds of a different type and/or formulation auxiliaires and/or additives customary in crop protection, or they may be employed together with these. Preference is given to herbicide combinations comprising a synergistically effective amount of components (A), (B) and (C).

In a preferred embodiment, the herbicide combinations according to the invention have synergistic effects. The synergistic effects are observed, for example, when the active compounds (A), (B) and (C) are applied together, but they can frequently also be observed when the compounds are applied as a split application over time. Another possibility is the application of the individual herbicides or the herbicide combinations in a plurality of portions (sequential application), for example after pre-emergence applications, followed by post-emergence applications or after early post-emergence applications, followed by applications at medium or late post-emergence.

Preferred is the simultaneous or nearly simultaneous application of the active compounds of the herbicide combination according to the invention. In a preferred embodiment, the herbicide combinations according to the invention are mixtures or compositions comprising the active compounds (A), (B) and (C) together.

The synergistic effects allow the application rates of the individual active compounds to be reduced, a more potent action at the same application rate, the control of hitherto uncontrollable species (activity gaps), an extended application period and/or a reduced number of individual applications required and—as a result for the user—more advantageous weed control systems both from an economical and ecological point of view.

The above mentioned formulae (I) and (II) include all stereoisomers and their mixtures, in particular also racemic mixtures and—if enantiomers are possible—the respective biologically active enantiomer. Compounds of the formulae (I) and (II) and their salts and also their preparation are described, for example, in WO 92/13845 and WO 95/10507. Preferred compounds of the formulae (I) and their salts are methyl 2-[3-(4,6-dimethoxypyrimidin-2-yl)ureidosulfonyl]-4-methanesulfone-aminomethyl-benzoate (mesosulfuron-methyl, A1-1) and its salts, such as the sodium salt (mesosulfuron-methyl-sodium, A1-2) (see, for example, WO 95/10507 and Agrow No. 347, 3.3.2000, page 22 (PJB Publications Ltd. 2000). Preferred compounds of the formula (II) and their salts are 3-(4-methoxy-6-methyl-1,3,5-triazin-2-yl)-1-(2-methoxycarbonyl-5-iodophenyl-sulfonyl)urea (iodosulfuron-methyl, B1-1) and its salts, such as the sodium salt idodosulfuron-methyl-sodium, B1-2) (see, for example, WO 92/13845 and PM, pp. 547-548).

Preferred (C) compounds are selected from
(C-1) methyl 4-[(4,5-dihydro-3-methoxy-4-methyl-5-oxo-1H-1,2,4-triazol-1-yl)carbonylsulfamoyl]-5-methylthio-phene-3-carboxylate, having the ISO name thienecarbazone-methyl (CAS No. 317815-83-1), (C1-1) described in WO 01/05788.

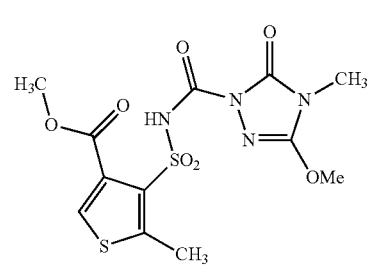

(III)

and its salts, preferably its sodium salt (C1-2);
(C-2) N-(5,7-dimethoxy[1,2,4]triazolo[1,5-a]pyrimidin-2-yl)-2-methoxy-4-(trifluoromethyl)-3-pyridinesulfonamide, having the ISO name pyroxsulam (CAS no. 422556-08-9) (C2-1) and its salts or esters;

(C-3) 4-amino-3-chloro-6-(4-chloro-2-fluoro-3-methoxyphenyl)-2-pyridinecarboxylic acid, having the ISO name halauxifen (CAS no. 943832-60-8) (C3-1) and its salts or esters, preferably halauxifen-methyl ester (CAS no. 943831-98-9) (C3-2).

(C-4) 8-(2,6-diethyl-4-methylphenyl)-1,2,4,5-tetrahydro-7-oxo-7H-pyrazolo[1,2-d][1,4,5]oxadiazepin-9-yl 2,2-dimethylpropanoate having the ISO name pinoxaden (CAS no. 243973-20-8) (C4-1) and its salts or esters;

(C-5) 3-[[[5-(difluoromethoxy)-1-methyl-3-(trifluoromethyl)-1H-pyrazol-4-yl]methyl]sulfonyl]-4,5-dihydro-5,5-dimethylisoxazole having the ISO name pyroxasulfone (CAS no. 447399-55-5) (C5-1) and its salts or esters;

The abovementioned active compounds (A) and (B) and their salts are capable of inhibiting the enzyme acetolactate synthase (ALS) and thus protein synthesis in plants. The application rate of the active compounds of the formulae (A), (B) and (C) and/or their salts can be varied within a wide range, for example between 0.001 and 0.5 kg of AS/ha, preferably 0.010 and 0.100 kg of AS/ha, most preferably 0.035 to 0.05. kgAS/ha. The abbreviation AS/ha used in this description means "active substance per hectare", based on 100% active compound. In the case of applications at application rates of 0.01 to 0.2 kg of AS/ha of the active compounds (A) and (B) and their salts, preferably the active compounds (A1-1), (A1-2), (B1-1) and (B1-2), a relatively broad spectrum of annual and perennial broad-leaved weeds, weed grasses and Cyperacea is controlled pre- and post-emergence. In the combinations according to the invention, the application rates are generally lower, for example in the range from 0.1 to 100 g of AS/ha, preferably from 0.5 to 50 g of AS/ha.

In a preferred embodiment of the invention (C-1) thienecarbazone-methyl and/or its salts is applied at a rate of 0.005 to 0.020 kg of AS/ha, preferably 0.007 to 0.015 kg of AS/ha, most preferably 0.0075 to 0.010 kg of AS/ha;

(C-2) pyroxsulam and/or its salts or esters is applied at a rate of 0.005 to 0.050 kg of AS/ha, preferably 0.010 to 0.025 kg of AS/ha, most preferably 0.018 to 0.020 kg of AS/ha;

(C-3) halauxifen and/or its salts or esters is applied at a rate of 0.005 to 0.020 kg of AS/ha, preferably 0.005 to 0.015 kg of AS/ha, most preferably 0.008 to 0.010 kg of AS/ha;

(C-4) pinoxaden and/or its salts or esters is applied at a rate of 0.005 to 0.100 kg of AS/ha, preferably 0.050 to 0.080 kg of AS/ha, most preferably 0.060 to 0.065 kg of AS/ha;

(C-5) pyroxasulfone and/or its salts or esters is applied at a rate of 0.050 to 0.500 kg of AS/ha, preferably 0.080 to 0.250 kg of AS/ha, most preferably 0.100 to 0.150 kg of AS/ha.

The active compounds can generally be formulated as water-soluble wettable powders (WP), water-dispersible granules (WDG), water-emulsifiable granules (WEG), suspoemulsion (SE), oil suspension concentrate (SC) or oil dispersion (OD).

The weight ratio of the components A and B to one another is between 10:1 to 1:10 preferably 8:1 to 1:2, most preferably 5:1 to 1:1.

The ratios of the application rates (A+B):C which are generally used are stated hereinabove and identify the weight ratio of the two components (A+B) and C to each other is generally 5:1 to 1:5, preferably 4:1 to 1:2, and most preferably 1.5:1 to 1:1.

The preferred weight ratio of the two components (A+B) and (C-1) to each other is advantageously 5:1 to 1:3, preferably 4:1 to 1:2, more preferably 3:1 to 1:1, and most preferably 5:2 to 3:2.

The preferred weight ratio of the two components (A+B) and (C-2) to each other is advantageously 3:1 to 1:4, preferably 2:1 to 1:3, more preferably 3:2 to 2:5, and most preferably 1:1 to 1:2.

The preferred weight ratio of the two components (A+B) and (C-4) to each other is advantageously 2:1 to 1:5, preferably 3:2 to 1:5, more preferably 1:1 to 1:4, and most preferably 1:2 to 1:4.

For use of the active compounds of the formulae (I) and (II) or their salts in plant crops, it is expedient, depending on the plant crop, to apply a safener from certain application rates upward in order to reduce or to avoid possible damage to the crop plants. Examples of suitable safeners are those which have a safener action in combination with sulfonylurea herbicides, preferably phenylsulfonylureas. Suitable safeners are disclosed in WO-A-96/14747 and the literature cited therein.

The following groups of compounds are examples of suitable safeners for the abovementioned herbicidally active compounds (A) and (B):

a) Compounds of the dichlorophenylpyrazoline-3-carboxylic acid (S1) type, preferably compounds such as ethyl 1-(2,4-dichlorophenyl)-5-(ethoxycarbonyl)-5-methyl-2-pyrazoline-3-carboxylate (S1-1, mefenpyr-diethyl, PM, pp. 594-595), and related compounds as they are described for example in WO 91/07874 and PM (pp. 594-595).

b) Dichlorophenylpyrazolecarboxylic acid derivatives, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethyl-ethyl)pyrazole-3-carboxylate (S1-4), ethyl 1-(2,4-dichlorophenyl)-5-phenylpyrazole-3-carboxylate (S1-5) and related compounds as are described in EP-A-333 131 and EP-A-269 806.

c) Compounds of the triazolecarboxylic acid (S1) type, preferably compounds such as fenchlorazole, i.e. ethyl 1-(2,4-dichlorophenyl)-5-trichloromethyl-(1H)-1,2,4-triazole-3-carboxylate (S1-6) and related compounds (see EP-A-174 562 and EP-A-346 620).

d) Compounds of the 5-benzyl- or 5-phenyl-2-isoxazoline-3-carboxylic acid type or of the 5,5-diphenyl-2-isoxazoline-3-carboxylic acid type, preferably compounds such as ethyl 5-(2,4-dichlorobenzyl)-2-isoxazoline-3-carboxylate (S1-7) or ethyl 5-phenyl-2-isoxazoline-3-carboxylate (S1-8) and related compounds as are described in WO 91/08202, or of ethyl 5,5-diphenyl-2-isoxazoline-3-carboxylate (S1-9, isoxadifen-ethyl) or n-propyl 5,5-diphenyl-2-isoxazoline-3-carboxylate (S1-10) or ethyl 5-(4-fluorophenyl)-5-phenyl-2-isoxazoline-3-carboxylate (51-11), as are described in patent application (WO-A-95/07897).

e) Compounds of the 8-quinoline oxyacetic acid (S2) type, preferably 1-methylhex-1-yl (5-chloro-8-quinolinoxy)acetate (S2-1, cloquintocet-mexyl, e.g. PM (pp. 195-196), (1,3-dimethylbut-1-yl) (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl (5-chloro-8-quinolinoxy)acetate (S2-6), allyl (5-chloro-8-quinolinoxy)acetate (S2-7),
2-(2-propylideneiminooxy)-1-ethyl (5-chloro-8-quinolinoxy)acetate (S2-8),
2-oxoprop-1-yl (5-chloro-8-quinolinoxy)acetate (S2-9)
and related compounds as are described in EP-A-86 750, EP-A-94 349 and EP-A-191 736 or EP-A-0 492 366.

f) Compounds of the (5-chloro-8-quinolinoxy)malonic acid type, preferably compounds such as diethyl (5-chloro-8-quinolinoxy)malonate, diallyl (5-chloro-8-quinolinoxy) malonate, methyl ethyl (5-chloro-8-quinolinoxy)-malonate and related compounds as are described in EP-A-0 582 198.

g) Active compounds of the phenoxyacetic acids, phenoxypropionic acids or aromatic carboxylic acids type, such as, for example, 2,4-dichlorophenoxyacetic acid (and esters) (2,4-D), 4-chloro-2-methylphenoxypropionic esters (mecoprop), MCPA or 3,6-dichloro-2-methoxybenzoic acid (and esters) (dicamba).

In many cases, the abovementioned safeners are also suitable for active compounds of group (C). In addition, the following safeners are suitable for the herbicide combinations according to the invention:

h) active compounds of the pyrimidine type, such as, for example, "fenclorim" (PM, pp. 386-387) (=4,6-dichloro-2-phenylpyrimidine), i) active compounds of the dichloroacetamide type, which are frequently used as pre-emergence safeners (soil-acting safeners) such as, for example,
"dichloromid" (PM, pp. 270-271) (=N,N-diallyl-2,2-dichloroacetamide),
"AR-29148" (=3-dichloroacetyl-2,2,5-trimethyl-1,3-oxazolidone by Stauffer),
"benoxacor" (PM, pp. 74-75) (=4-dichloroacetyl-3,4-dihydro-3-methyl-2H-1,4-benzoxazine),
"APPG-1292" (=N-allyl-N[(1,3-dioxolan-2-yl)-methyl] dichloroacetamide by PPG Industries),
"ADK-24" (=N-allyl-N-[(allylaminocarbonyl)-methyl]-dichloroacetamide by Sagro-Chem),
"AAD-67" or "AMON 4660" (=3-dichloroacetyl-1-oxa-3-aza-spiro[4,5]decane by Nitrokemia or Monsanto),
"diclonon" or "ABAS145138" or "ALAB145138" (=(=3-dichloroacetyl-2,5,5-trimethyl-1,3-diazabicyclo[4.3.0] nonane by BASF) and
"furilazol" or "AMON 13900" (see PM, 482-483) (=(RS)-3-dichloroacetyl-5-(2-furyl)-2,2-dimethyloxazolidone)

j) active compounds of the dichloroacetone derivatives type, such as, for example,
"AMG 191" (CAS Reg. No. 96420-72-3) (=2-dichloromethyl-2-methyl-1,3-dioxolane by Nitrokemia), k) active compounds of the oxyimino compounds type which are known as seed-dressing materials such as, for example,
"oxabetrinil" (PM, p. 689) (=(Z)-1,3-dioxolan-2-ylmethoxyimino(phenyl)acetonitrile, which is known as safener in seed dressing to prevent metolachlor damage,
"fluxofenim" (PM, pp. 467-468) (=1-(4-chlorophenyl)-2,2,2-trifluoro-1-ethanone O-(1,3-dioxolan-2-ylmethyl)-oxime, which is known as safener in seed dressing to prevent metolachlor damage, and
"cyometrinil" or "A-CGA-43089" (PM, p. 983) (=(Z)-cyanomethoxyimino(phenyl)acetonitrile, which is known as safener in seed dressing to prevent metolachlor damage, l) active compounds of the thiazolecarboxylic esters type, which are known as seed-dressing materials, such as, for example,
"flurazol" (PM, pp. 450-451) (=benzyl 2-chloro-4-trifluoromethyl-1,3-thiazole-5-carboxylate), which is known as safener in seed dressing to prevent alachlor and metolachlor damage, m) active compounds of the naphthalenedicarboxylic acid derivatives type which are known as seed-dressing agents, such as, for example,
"naphthalic anhydride" (PM, pp. 1009-1010) (=1,8-naphthalenedicarboxylic anhydride), which is known as safener for maize in seed dressing to prevent thiocarbamate herbicide damage, n) active compounds of the chromaneacetic acid derivatives type, such as, for example,
"ACL 304415" (CAS Reg. No. 31541-57-8) (=2-84-carboxychroman-4-yl)acetic acid by American Cyanamid), o) active compounds which, in addition to a herbicidal action against harmful plants, also have a safener action on crop plants, such as, for example,
"dimepiperate" or "AMY-93" (PM, pp. 302-303) (=S-1-methyl-1-phenylethyl piperidine-1-carbothioate),
"daimuron" or "ASK 23" (PM, p. 247) (=1-(1-methyl-1-phenylethyl)-3-p-tolylurea), "cumyluron"="AJC-940" (=3-(2-chlorophenylmethyl)-1-(1-methyl-1-phenylethyl)urea, see JP-A-60087254),
"methoxyphenon" or "ANK 049" (=3,3'-dimethyl-4-methoxy-benzophenone),
"CSB" (=1-bromo-4-(chloromethylsulfonyl)benzene) (CAS Reg. No. 54091-06-4 by Kumiai).

The herbicides (A) and (B), if appropriate in the presence of safeners (the combination (A1-2)+(S1-1), for example, is commercially available as Sigma® OD, and the combination (A1-2)+(B1-2)+(S1-1) as Atlantis® WG), are suitable for controlling harmful plants in plant crops, for example in economically important crops such as cereals (such as wheat, barley, rye, oats, rice, corn, millet), sugar beet, sugar cane, oilseed rape, cotton and soybeans. Of particular interest is the application in monocotyledonous crops such as cereals, for example wheat, barley, rye, oats, in particular hybrids thereof such as triticale, rice, corn and millet. These crops are also preferred for the combinations (A)+(B)+(C).

Also included according to the invention are those herbicide combinations which, in addition to components (A), (B) and (C), also comprise one or more further agrochemically active compounds of a different structure, such as herbicides, insecticides, fungicides or safeners. To such combinations, the preferred conditions illustrated below in particular for combinations (A)+(B)+(C) according to the invention also primarily apply, if they comprise the combinations (A)+(B)+(C) according to the invention, and with respect to the combination (A)+(B)+(C) in question.

Of particular interest are herbicidal compositions according to the present invention and the use of herbicidal compositions according to the present invention comprising the following compounds (A)+(B)+(C), preferably mixtures or compositions comprising the active compounds (A), (B) and (C) together:
(A1-1)+(B1-1)+(C1-1), (A1-2)+(B1-1)+(C1-1);
(A1-1)+(B1-2)+(C1-1); (A1-2)+(B1-2)+(C1-1);
(A1-1)+(B1-1)+(C1-2), (A1-2)+(B1-1)+(C1-2);
(A1-1)+(B1-2)+(C1-2); (A1-2)+(B1-2)+(C1-2);
(A1-1)+(B1-1)+(C2-1), (A1-2)+(B1-1)+(C2-1);
(A1-1)+(B1-2)+(C2-1); (A1-2)+(B1-2)+(C2-1);
(A1-1)+(B1-1)+(C3-1), (A1-2)+(B1-1)+(C3-1);

(A1-1)+(B1-2)+(C3-1); (A1-2)+(B1-2)+(C3-1);
(A1-1)+(B1-1)+(C3-2), (A1-2)+(B1-1)+(C3-2);
(A1-1)+(B1-2)+(C3-2); (A1-2)+(B1-2)+(C3-2);
(A1-1)+(B1-1)+(C4-1), (A1-2)+(B1-1)+(C4-1);
(A1-1)+(B1-2)+(C4-1); (A1-2)+(B1-2)+(C4-1);
(A1-1)+(B1-1)+(C5-1), (A1-2)+(B1-1)+(C5-1);
(A1-1)+(B1-2)+(C5-1); (A1-2)+(B1-2)+(C5-1).

In addition, each of the herbicide combinations mentioned above (preferably the mixtures or compositions comprising the active compounds (A), (B) and (C) together) may additionally comprise one or more safeners, in particular a safener such as mefenpyr-diethyl (S1-1), isoxadifen-ethyl (S1-9) and cloquintocet-mexyl (S2-1). Preference is in each case given to the ranges of application rates and ratios of application rates mentioned above. Examples of this are the herbicide combinations listed below.

(A1-1)+(B1-1)+(C1-1)+(S1-1), (A1-2)+(B1-1)+(C1-1)+(S1-1);
(A1-1)+(B1-2)+(C1-1)+(S1-1); (A1-2)+(B1-2)+(C1-1)+(S1-1);
(A1-1)+(B1-1)+(C1-2)+(S1-1), (A1-2)+(B1-1)+(C1-2)+(S1-1);
(A1-1)+(B1-2)+(C1-2)+(S1-1); (A1-2)+(B1-2)+(C1-2)+(S1-1);
(A1-1)+(B1-1)+(C2-1)+(S1-1), (A1-2)+(B1-1)+(C2-1)+(S1-1);
(A1-1)+(B1-2)+(C2-1)+(S1-1); (A1-2)+(B1-2)+(C2-1)+(S1-1);
(A1-1)+(B1-1)+(C3-1)+(S1-1), (A1-2)+(B1-1)+(C3-1)+(S1-1);
(A1-1)+(B1-2)+(C3-1)+(S1-1); (A1-2)+(B1-2)+(C3-1)+(S1-1);
(A1-1)+(B1-1)+(C3-2)+(S1-1), (A1-2)+(B1-1)+(C3-2)+(S1-1);
(A1-1)+(B1-2)+(C3-2)+(S1-1); (A1-2)+(B1-2)+(C3-2)+(S1-1);
(A1-1)+(B1-1)+(C4-1)+(S1-1), (A1-2)+(B1-1)+(C4-1)+(S1-1);
(A1-1)+(B1-2)+(C4-1)+(S1-1); (A1-2)+(B1-2)+(C4-1)+(S1-1);
(A1-1)+(B1-1)+(C5-1)+(S1-1), (A1-2)+(B1-1)+(C5-1)+(S1-1);
(A1-1)+(B1-2)+(C5-1)+(S1-1); (A1-2)+(B1-2)+(C5-1)+(S1-1);
(A1-1)+(B1-1)+(C1-1)+(S1-9), (A1-2)+(B1-1)+(C1-1)+(S1-9);
(A1-1)+(B1-2)+(C1-1)+(S1-9); (A1-2)+(B1-2)+(C1-1)+(S1-9);
(A1-1)+(B1-1)+(C1-2)+(S1-9); (A1-2)+(B1-1)+(C1-2)+(S1-9);
(A1-1)+(B1-2)+(C1-2)+(S1-9); (A1-2)+(B1-2)+(C1-2)+(S1-9);
(A1-1)+(B1-1)+(C2-1)+(S1-9); (A1-2)+(B1-1)+(C2-1)+(S1-9);
(A1-1)+(B1-2)+(C2-1)+(S1-9); (A1-2)+(B1-2)+(C2-1)+(S1-9);
(A1-1)+(B1-1)+(C3-1)+(S1-9); (A1-2)+(B1-1)+(C3-1)+(S1-9);
(A1-1)+(B1-2)+(C3-1)+(S1-9); (A1-2)+(B1-2)+(C3-1)+(S1-9);
(A1-1)+(B1-1)+(C3-2)+(S1-9); (A1-2)+(B1-1)+(C3-2)+(S1-9);
(A1-1)+(B1-2)+(C3-2)+(S1-9); (A1-2)+(B1-2)+(C3-2)+(S1-9);
(A1-1)+(B1-1)+(C4-1)+(S1-9); (A1-2)+(B1-1)+(C4-1)+(S1-9);
(A1-1)+(B1-2)+(C4-1)+(S1-9); (A1-2)+(B1-2)+(C4-1)+(S1-9);
(A1-1)+(B1-1)+(C5-1)+(S1-9); (A1-2)+(B1-1)+(C5-1)+(S1-9);
(A1-1)+(B1-2)+(C5-1)+(S1-9); (A1-2)+(B1-2)+(C5-1)+(S1-9);
(A1-1)+(B1-1)+(C1-1)+(S2-1); (A1-2)+(B1-1)+(C1-1)+(S2-1);
(A1-1)+(B1-2)+(C1-1)+(S2-1); (A1-2)+(B1-2)+(C1-1)+(S2-1);
(A1-1)+(B1-1)+(C1-2)+(S2-1); (A1-2)+(B1-1)+(C1-2)+(S2-1);
(A1-1)+(B1-2)+(C1-2)+(S2-1); (A1-2)+(B1-2)+(C1-2)+(S2-1);
(A1-1)+(B1-1)+(C2-1)+(S2-1); (A1-2)+(B1-1)+(C2-1)+(S2-1);
(A1-1)+(B1-2)+(C2-1)+(S2-1); (A1-2)+(B1-2)+(C2-1)+(S2-1);
(A1-1)+(B1-1)+(C3-1)+(S2-1); (A1-2)+(B1-1)+(C3-1)+(S2-1);
(A1-1)+(B1-2)+(C3-1)+(S2-1); (A1-2)+(B1-2)+(C3-1)+(S2-1);
(A1-1)+(B1-1)+(C3-2)+(S2-1); (A1-2)+(B1-1)+(C3-2)+(S2-1);
(A1-1)+(B1-2)+(C3-2)+(S2-1); (A1-2)+(B1-2)+(C3-2)+(S2-1);
(A1-1)+(B1-1)+(C4-1)+(S2-1); (A1-2)+(B1-1)+(C4-1)+(S2-1);
(A1-1)+(B1-2)+(C4-1)+(S2-1); (A1-2)+(B1-2)+(C4-1)+(S2-1);
(A1-1)+(B1-1)+(C5-1)+(S2-1); (A1-2)+(B1-1)+(C5-1)+(S2-1);
(A1-1)+(B1-2)+(C5-1)+(S2-1); (A1-2)+(B1-2)+(C5-1)+(S2-1).

It may be advantageous to combine one or more herbicides (A) with one or more herbicides (B) and one or more herbicides (C), for example a herbicide (A) with a herbicide (B) and one or more herbicides (C). Herbicide combinations according to the invention with a plurality of herbicide C) are, for example, those which comprise, as component C), the following herbicide combinations: C1+C2, which preferably comprise, as components (A) and (B), the compounds (A1-1)+(B1-1), (A1-1)+(B1-2), (A1-2)+(B1-1) or (A1-2)+(B1-2), in particular (A1-1)+(B1-2), and which may additionally comprise a safener, such as (S1-1), (S1-9) or (S2-1), in particular (S1-1). Furthermore, the combinations of herbicides according to the invention can be used together with other agrochemically active compounds, for example from the group of the safeners, fungicides, herbicides, insecticides and plant growth regulators, or with formulation auxiliaries and additives customary in crop protection. Additives are, for example, fertilizers and colorants. Preference is in each case given to the ratios of application rates and ranges of application rates mentioned above.

The combinations according to the invention (=herbicidal compositions) have an outstanding herbicidal activity against a broad spectrum of economically important monocotyledonous and dicotyledonous harmful plants. The active compounds also act efficiently on perennial weeds which produce shoots from rhizomes, rootstocks or other perennial organs and which are difficult to control. In this context, it does not matter whether the substances are applied before sowing, pre-emergence or post-emergence. Post-emergence application, or early post-sowing pre-emergence application, is preferred.

Specifically, examples may be mentioned of some representatives of the monocotyledonous and dicotyledonous weed flora which can be controlled by the combinations according to the invention, without the enumeration being a restriction to certain species.

Examples of weed species on which the herbicidal compositions act efficiently are, from amongst the monocotyledonous weed species, for example *Apera spica venti*, *Avena* spp., *Alopecurus* spp., *Brachiaria* spp., *Digitaria* spp., *Lolium* spp., *Equinochloa* spp., *Panicum* spp., *Phalaris* spp., *Poa* spp., *Setaria* spp. and also *Bromus* spp., such as *Bromus catharticus*, *Bromus secalinus*, *Bromus erectus*, *Bromus tectorum* and *Bromus japonicus*, and *Cyperus* species from the annual group, and, amongst the perennial species, *Agropyron*, *Cynodon*, *Imperata* and *Sorghum* and also perennial *Cyperus* species.

In the case of the dicotyledonous weed species, the spectrum of action extends to species such as, for example, *Abutilon* spp., *Amaranthus* spp., *Chenopodium* spp., *Chrysanthemum* spp., *Galium* spp. such as *Galium aparine*, *Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., amongst the annuals, and *Convolvulus*, *Cirsium*, *Rumex* and *Artemisia* in the case of the perennial weeds.

If the herbicide combinations according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

The herbicidal compositions according to the invention are distinguished by a rapidly commencing and long-lasting herbicidal action. As a rule, the rainfastness of the active compounds in the combinations according to the invention is advantageous. A particular advantage is that the dosages of the compounds (A), (B) and (C), which are used in the combinations and are effective, can be adjusted to such a low quantity that their soil action is optimally low. Not only does this allow them to be employed in sensitive crops in the first place, but groundwater and surface water contaminations are virtually avoided. The active-ingredient combination according to the invention allows the application rate of the active compounds required to be reduced considerably.

In a preferred embodiment, when herbicides of the type (A)+(B)+(C) are used jointly, superadditive (=synergistic) effects are observed. This means that the effect in the combinations exceeds the expected total of the effects of the individual herbicides employed. The synergistic effects allow the application rate to be reduced, a broader spectrum of broad-leaved weeds and grass weeds to be controlled, the herbicidal action to take place more rapidly, the duration of action to be longer, the harmful plants to be controlled better while using only one, or few, applications, and the application period which is possible to be extended. In some cases, the use of the compositions also reduces the amount of harmful ingredients, such as nitrogen or oleic acid, and their introduction into the soil.

The abovementioned properties and advantages are of benefit for weed control practice to keep agricultural crops free from undesired competing plants and thus to safeguard and/or increase the yields from the qualitative and quantitative point of view. These novel combinations markedly exceed the technical state of the art with a view to the properties described.

While the combinations according to the invention have an outstanding herbicidal activity against monocotyledonous and dicotyledonous weeds, the crop plants are damaged only to a minor extent, if at all.

Moreover, some of the compositions according to the invention have outstanding growth-regulatory properties on the crop plants. They engage in the plants' metabolism in a regulatory manner and can thus be employed for provoking directed effects on plant constituents and to facilitate harvesting such as for example by triggering desiccation and stunted growth. Moreover, they are also suitable for the general control and inhibition of undesired vegetative growth without simultaneously destroying the plants. An inhibition of vegetative growth is very important in a large number of monocotyledonous and dicotyledonous crops since yield losses as a result of lodging can thus be reduced, or prevented completely.

Owing to their herbicidal and plant-growth-regulatory properties, the compositions according to the invention can be employed for controlling harmful plants in genetically modified crop plants or crop plants obtained by mutation/selection. These crop plants are distinguished as a rule by particular, advantageous properties, such as resistances to herbicidal compositions or resistances to plant diseases or causative agents of plant diseases such as particular insects or microorganisms such as fungi, bacteria or viruses. Other particular properties relate, for example, to the harvested material with regard to quantity, quality, storability, composition and specific constituents. Thus, for example, transgenic plants are known whose starch content is increased or whose starch quality is altered, or those where the harvested material has a different fatty acid composition.

Conventional methods of generating novel plants which have modified properties in comparison to plants occurring to date consist, for example, in traditional breeding methods and the generation of mutants (see, for example, U.S. Pat. No. 5,162,602; U.S. Pat. No. 4,761,373; U.S. Pat. No. 4,443,971). Alternatively, novel plants with altered properties can be generated with the aid of recombinant methods (see, for example, EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which exhibit resistances to other herbicides, for example to sulfonylureas (EP-A-0257993, U.S. Pat. No. 5,013,659), transgenic crop plants with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of techniques in molecular biology are known in principle with the aid of which novel transgenic plants with modified properties can be generated: see, for example, Sambrook et al., 1989, Molecular Cloning, A Laboratory Manual, $2^{nd}$ Edition, Cold Spring Harbor Laboratory Press, Cold Spring Harbor, N.Y.; or Winnacker "Gene and Klone", VCH Weinheim $2^{nd}$ Edition 1996 or Christou, "Trends in Plant Science" 1 (1996) 423-431).

To carry out such recombinant manipulations, nucleic acid molecules which allow mutagenesis or sequence changes by recombination of DNA sequences can be introduced into plasmids. For example, the abovementioned standard methods allow base exchanges to be carried out, subsequences to be removed, or natural or synthetic sequences to be added. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribosome which specifically cleaves transcripts of the abovementioned gene product.

To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the encoding sequences of a gene product, but are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated by known techniques to give rise to intact plants. In principle, the transgenic plants can be plants of any desired plant species, i.e. not only monocotyledonous, but also dicotyledonous, plants. Thus, transgenic plants can be obtained whose properties are altered by overexpression, suppression or inhibition of homologous (=natural) genes or gene sequences or the expression of heterologous (=foreign) genes or gene sequences.

The invention therefore also relates to a method of controlling undesired vegetation (e.g. harmful plants), preferably in plant crops such as cereals (e.g. wheat, barley, rye, oats, hybrids thereof such as triticale, rice, corn, millet), sugar beet, sugar cane, oilseed rape, cotton and soybeans, especially preferably in monocotyledonous crops such as cereals, for example wheat, barley, rye, oats, hybrids thereof such as triticale, rice, corn and millet, which comprises applying one or more herbicides of type (A) together with one or more herbicides of type (B) and one or more herbicides of type (C) jointly or separately, for example by the pre-emergence method, by the post-emergence method or by the pre-emergence and the post-emergence method, to the plants, for example harmful plants, parts of these plants, plant seeds or the area where the plants grow, for example the area under cultivation.

The plant crops can also have been genetically modified or been obtained by mutation selection and are preferably tolerant to acetolactate synthase (ALS) inhibitors.

The invention also relates to the use of the novel combinations of compounds (A)+(B)+(C) for controlling harmful plants, preferably in plant crops.

The herbicidal compositions according to the invention can also be used non-selectively for controlling unwanted vegetation, for example in plantation crops, in the borders of paths, in squares, in industrial plants or in railroad installations.

The active compound combinations according to the invention can exist not only as mixed formulations of the components (A), (B) and (C), if appropriate together with further agrochemically active compounds, additives and/or customary formulation auxiliaries, which are then applied in the customary manner as a dilution with water, but also as so-called tank mixes by jointly diluting the separately formulated, or partially separately formulated, components with water.

The compounds (A), (B) and (C) or their combinations can be formulated in various ways, depending on the prevailing biological and/or chemical-physical parameters. The following are examples of general possibilities for formulations: wettable powders (WP), water-soluble concentrates, emulsifiable concentrates (EC), aqueous solutions (SL), emulsions (EW) such as oil-in-water and water-in-oil emulsions, sprayable solutions or emulsions, suspension concentrates (SC), oil dispersions (OD), oil- or water-based dispersions, suspoemulsions, dusts (DP), seed-dressing materials, granules for soil application or for broadcasting, or water-dispersible granules (WG), ULV formulations, microcapsules or waxes.

The individual formulation types are known in principle and are described for example, in: Winnacker-Küchler, "Chemische Technologie", Volume 7, C. Hauser Verlag Munich, 4$^{th}$ Edition, 1986; van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are also known and are described, for example, in Watkins, "Handbook of Insecticide Dust Diluents and Carriers", 2nd Ed., Darland Books, Caldwell N.J.; H.v. Olphen, "Introduction to Clay Colloid Chemistry"; 2nd Ed., J. Wiley & Sons, N.Y. Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesellschaft, Stuttgart 1976, Winnacker-Küchler, "Chemische Technologie", Volume 7, C. Hauser Verlag Munich, 4$^{th}$ Edition 1986.

Based on these formulations, combinations with other agrochemically active substances, such as other herbicides, fungicides or insecticides, and with safeners, fertilizers and/or growth regulators, may also be prepared, for example in the form of a readymix or a tank mix.

Wettable powders (sprayable powders) are products which are uniformly dispersible in water and which, besides the active compound, also comprise ionic or nonionic surfactants (wetters, dispersants), for example polyoxethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoyl-methyltauride, in addition to a diluent or inert material.

Emulsifiable concentrates are prepared by dissolving the active compound in an organic solvent, for example butanol, cyclohexanone, dimethylformamide, xylene or else higher-boiling aromatics or hydrocarbons with addition of one or more ionic or nonionic surfactants (emulsifiers). Examples of emulsifiers which may be used are: calcium salts of alkylarylsulfonic acids, such as calcium dodecylbenzene sulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan fatty acid esters, polyoxyethylene sorbitan fatty acid esters or polyoxethylene sorbitol esters.

Dusts are obtained by grinding the active compound with finely divided solid materials, for example talc, natural clays such as kaolin, bentonite and pyrophyllite, or diatomaceous earth.

Suspension concentrates (SC) can be water- or oil-based. They can be prepared, for example, by wet grinding by means of commercially available bead mills and, if appropriate, addition of further surfactants as they have already been mentioned for example above in the case of the other formulation types.

Emulsions, for example oil-in-water emulsions (EW), can be prepared for example by means of stirrers, colloid mills and/or static mixers using aqueous organic solvents and, if appropriate, further surfactants as have already been mentioned for example above in the case of the other formulation types.

Granules can be prepared either by spraying the active compound onto adsorptive, granulated inert material or by applying active compound concentrates to the surface of carriers such as sand, kaolinites or granulated inert material with the aid of binders, for example polyvinyl alcohol, sodium polyacrylate or else mineral oils. Suitable active compounds may also be granulated in the manner conventionally used for the production of fertilizer granules, if desired in a mixture with fertilizers. As a rule, water-dispersible granules are prepared by customary processes such as spray drying, fluidized-bed granulation, disk granulation, mixing with high-speed mixers and extrusion without solid inert material. Regarding the production of disk granules, fluidized-bed granules, extruder granules and spray granules, see, for example, the methods in "Spray-Drying Handbook" 3rd ed. 1979, G. Goodwin Ltd., London; J. E. Browning, "Agglomeration", Chemical and Engineering 1967, page 147 et seq; "Perry's Chemical Engineer's Handbook", 5th Ed., McGraw-Hill, New York 1973, pp. 8-57.

As regards further details on the formulation of crop protection products, see, for example, G. C. Klingmam, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

As a rule, the agrochemical formulations comprise 0.1 to 99 percent by weight, in particular 2 to 95% by weight, of active compounds of the types A and/or B and/or C, the following concentrations being customary, depending on the type of formulation:

The active compound concentration in wettable powders is, for example, approximately 10 to 95% by weight, the remainder to 100% by weight being composed of customary formulation constituents. In the case of emulsifiable concentrates, the active compound concentration may amount to, for example, 5 to 80% by weight. Formulations in the form of dusts comprise, in most cases, 5 to 20% by weight of active compound, sprayable solutions approximately 0.2 to 25% by weight of active compound. In the case of granules such as dispersible granules, the active compound content depends partly on whether the active compound is present in liquid or solid form and on which granulation auxiliaries and fillers are being used. As a rule, the content amounts to between 10 and 90% by weight in the case of the water-dispersible granules.

In addition, the abovementioned active compound formulations may comprise, if appropriate, the conventional adhesives, wetters, dispersants, emulsifiers, preservatives, antifreeze agents, solvents, fillers, colorants, carriers, antifoams, evaporation inhibitors, pH regulators or viscosity regulators.

The herbicidal action of the herbicide combinations according to the invention can be improved, for example, by surfactants, preferably by wetters from the group of the fatty alcohol polyglycol ethers. The fatty alcohol polyglycol ethers preferable contain 10-18 carbon atoms in the fatty alcohol radical and 2-20 ethylene oxide units in the polyglycol ether moiety. The fatty alcohol polyglycol ethers can be nonionic or ionic, for example in the form of fatty alcohol polyglycol ethers sulfates, which can be used, for example, as alkali metal salts (e.g. sodium salts or potassium salts) or ammonium salts, but also as alkaline earth metal salts such as magnesium salts, such as sodium $C_{12}/C_{14}$-fatty alcohol diglycol ether sulfate (Genapol® LRO, Clariant); see, for example, EP-A-0476555, EP-A-0048436, EP-A-0336151 or U.S. Pat. No. 4,400,196 and also Proc. EWRS Symp. "Factors Affecting Herbicidal Activity and Selectivity", 227-232 (1988). Nonionic fatty alcohol polyglycol ethers are, for example, ($C_{10}$-$C_{18}$)—, preferably ($C_{10}$-$C_{14}$)-fatty alcohol polyglycol ethers containing 2-20, preferably 3-15, ethylene oxide units (e.g. isotridecyl alcohol polyglycol ether), for example from the Genapol® series, such as Genapol® X-030, Genapol® X-060, Genapol® X-080 or Genapol® X-150 (all from Clariant GmbH).

The present invention furthermore embraces the combination of herbicides (A), (B) and (C) with the wetting agents mentioned above from the group of the fatty alcohol polyglycolethers which preferably contain 10-18 carbon atoms in the fatty alcohol radical and 2-20 ethylene oxide units in the polyglycol ether moiety and which can be present in nonionic or ionic form (for example as fatty alcohol polyglycol ether sulfates). Preference is given to $C_{12}/C_{14}$-fatty alcohol diglycol ether sulfate sodium (Genapol® LRO, Clariant); and isotridecyl alcohol polyglycol ether with 3-15 ethylene oxide units, for example from the Genapol® X series, such as Genapol® X-030, Genapol® X-060, Genapol® X-080 or Genapol® X-150 (all from Clariant GmbH). It is furthermore known that fatty alcohol polyglycol ethers such as nonionic or ionic fatty alcohol polyglycol ethers (for example fatty alcohol polyglycol ether sulfates) are also suitable for use as penetrants and activity enhancers for a number of other herbicides, inter alia also for herbicides from the group of the imidazolinones (see, for example, EP-A-0502014).

Moreover, it is known that fatty alcohol polyglycol ethers such as nonionic or ionic fatty alcohol polyglycol ethers (for example fatty alcohol polyglycol ether sulfates) are also suitable as penetrants and synergists for a number of other herbicides, inter alia also herbicides from the group of the imidazolinones; (see, for example, EP-A-0502014).

The herbicidal effect of the herbicide combinations according to the invention can also be increased using vegetable oils. The term vegetable oils is to be understood as meaning oils from oil-plant species, such as soya oil, rapeseed oil, corn oil, sunflower oil, cottonseed oil, linseed oil, coconut oil, palm oil, safflower oil or castor oil, in particular rapeseed oil, and their transesterification products, for example alkyl esters, such as rapeseed oil methyl ester or rapeseed oil ethyl ester.

The vegetable oils are preferably esters of $C_{10}$-$C_{22}$—, preferably $C_{12}$-$C_{20}$-fatty acids. The $C_{10}$-$C_{22}$-fatty acid esters are, for example, esters of unsaturated or saturated $C_{10}$-$C_{22}$-fatty acids, in particular those with an even number of carbon atoms, for example erucic acid, lauric acid, palmitic acid and, in particular, $C_{18}$-fatty acids such as stearic acid, oleic acid, linoleic acid or linolenic acid.

Examples of $C_{10}$-$C_{22}$-fatty acid esters are esters obtained by reacting glycerol or glycol with the $C_{10}$-$C_{22}$-fatty acids as they exist, for example in oils from oil-plant species, or $C_1$-$C_{20}$-alkyl-$C_{10}$-$C_{22}$-fatty acid esters as can be obtained, for example, by transesterification of the abovementioned glycerol- or glycol-$C_{10}$-$C_{22}$-fatty acid esters with $C_1$-$C_{20}$-alcohols (for example methanol, ethanol, propanol or butanol). Transesterification can be carried out by known methods as are described, for example, in Römpp Chemie Lexikon, 9th edition, volume 2, page 1343, Thieme Verlag Stuttgart.

Preferred $C_1$-$C_{20}$-alkyl-$C_{10}$-$C_{22}$-fatty acid esters are the methyl, ethyl, propyl, butyl, 2-ethylhexyl and dodecyl esters. Preferred glycol- and glycerol-$C_{10}$-$C_{22}$-fatty acid esters are the uniform or mixed glycol esters and glycerol esters of $C_{10}$-$C_{22}$-fatty acids, in particular those fatty acids which have an even number of carbon atoms, for example erucic acid, lauric acid, palmitic acid and, in particular, $C_{18}$-fatty acids such as stearic acid, oleic acid, linolic acid or linolenic acid.

The vegetable oils can be present in the herbicidal compositions according to the invention for example in the form of commercially available oil-containing formulation additives, in particular those based on rapeseed oil such as Hasten® (Victorian Chemical Company, Australia, hereinbelow termed Hasten, main constituent: rapeseed oil ethyl ester), Actirob®B (Novance, France, hereinbelow termed ActirobB, main constituent: rapeseed oil methyl ester), Rako-Binol® (Bayer AG, Germany, termed Rako-Binol hereinbelow, main constituent: rapeseed oil), Renol® (Stefes, Germany, termed Renol hereinbelow, vegetable oil constituent: rapeseed oil methyl ester), or Stefes Mero® (Stefes, Germany, hereinbelow termed Mero, main constituent: rapeseed oil methyl ester).

In a further embodiment, the present invention embraces combinations of herbicides (A), (B) and (C) with the vegetable oils mentioned above, such as rapeseed oil, preferably in the form of commercially available oil-containing formulation additives, in particular those based on rapeseed oil such as Hasten® (Victorian Chemical Company, Australia, hereinbelow termed Hasten, main constituent: rapeseed oil ethyl ester), Actirob®B (Novance, France, hereinbelow termed ActirobB, main constituent: rapeseed oil methyl ester), Rako-Binol® (Bayer AG, Germany, termed Rako-Binol hereinbelow, main constituent: rapeseed oil), Renol® (Stefes, Germany, termed Renol hereinbelow, vegetable oil constituent: rapeseed oil methyl ester), or Stefes Mero® (Stefes, Germany, hereinbelow termed Mero, main constituent: rapeseed oil methyl ester).

For use, the formulations, which are present in commercially available form, are optionally diluted in the customary manner, for example using water in the case of wettable powders, emulsifiable concentrates, dispersions and water-dispersible granules. Preparations in the form of dusts, soil granules, granules for broadcasting and sprayable solutions are usually not diluted further with other inert substances prior to use.

The active compounds can be applied to the plants, parts of the plants, seeds of the plants or the area under cultivation (soil of a field), preferably to the green plants and parts of the plants and, if appropriate, additionally to the soil of the field.

One possible use is the joint application of the active compounds in the form of tank mixes, the concentrated formulations of the individual active compounds, in optical formulations, jointly being mixed with water in the tank and the resulting spray mixture being applied.

A joint herbicidal formulation of the combination according to the invention of the active compounds (A), (B) and (C) has the advantage of being easier to apply since the quantities of the components are already presented in the correct ratio to each other. Moreover, the adjuvants in the formulation can be matched optimally to each other.

A. GENERAL FORMULATION EXAMPLES a) A dust is obtained by mixing 10 parts by weight of an active compound/active compound mixture and 90 parts by weight of talc as inert material and comminuting the mixture in a hammer mill b) A wettable powder which is readily dispersible in water is obtained by mixing 25 parts by weight of an active compound/active compound mixture, 64 parts by weight of kaolin-containing quartz as inert material, 10 parts by weight of potassium lignosulfonate and 1 part by weight of sodium oleoylmethyltaurinate as wetter and dispersant, and grinding the mixture in a pinned-disk mill.

c) A dispersion concentrate which is readily dispersible in water is obtained by mixing 20 parts by weight of an active compound/active compound mixture with 6 parts by weight of alkylphenol polyglycol ether (® Triton X 207), 3 parts by weight of isotridecanol polyglycol ether (8 EO) and 71 parts by weight of paraffinic mineral oil (boiling range for example approx. 255 to 277° C.), and grinding the mixture in a ball mill to a fineness of below 5 microns.

d) An emulsifiable concentrate is obtained from 15 parts by weight of an active compound/active compound mixture, 75 parts by weight of cyclohexanone as solvent and 10 parts by weight of oxethylated nonylphenol as emulsifier.

e) Water-dispersible granules are obtained by mixing
    75 parts by weight of an active compound/active compound mixture,
    10 parts by weight of calcium lignosulfonate,
    5 parts by weight of sodium lauryl sulfate,
    3 parts by weight of polyvinyl alcohol and
    7 parts by weight of kaolin,
    grinding the mixture on a pinned-disk mill and granulating the powder in a fluidized bed by spraying on water as granulation liquid.

f) Water-dispersible granules are also obtained by homogenizing and precomminuting, in a colloid mill,
    25 parts by weight of an active compound/active compound mixture,
    5 parts by weight of sodium 2,2'-dinaphthylmethane-6,6'-disulfonate,
    2 parts by weight of sodium oleoylmethyltaurinate,
    1 part by weight of polyvinyl alcohol,
    17 parts by weight of calcium carbonate and
    50 parts by weight of water,
    subsequently grinding the mixture in a bead mill and atomizing and drying the resulting suspension in a spray tower by means of a single-substance nozzle.

A1. SPECIFIC FORMULATION EXAMPLES

A1.a A water-dispersible granules (WG) formulation was prepared containing the following active ingredients, the balance being inert materials:
    45 g/kg Mesosulfuron-methyl (A1-1)
    9 g/kg Iodosulfuron-methyl-sodium (B1-2)

22.5 g/kg Thienecarbazone-methyl (C1-1)
135 g/kg Mefenpyr-diethyl (S1-1)

A1.b An oil dispersion (OD) formulation was prepared containing the following active ingredients, the balance being inert materials:
10 g/l Mesosulfuron-methyl-sodium (A1-2)
2 g/l Iodosulfuron-methyl-sodium (B1-2)
5 g/l Thienecarbazone-methyl (C1-1)
30 g/l Mefenpyr-diethyl (S1-1)

B. BIOLOGICAL EXAMPLES

Herbicidal Action (Outdoor Trials)

The seeds or rhizome pieces of typical harmful plants were planted and grown under natural outdoor conditions. After the harmful plants had emerged, they were treated, as a rule at the 2- to 4-leaf stage, with various dosages of the compositions according to the invention at a water application rate of 100 to 400l/ha (converted).

After the treatment (approx. 4-6 weeks after application), the herbicidal activity of the active compounds or active compound mixtures was scored visually by comparing the treated plots with the untreated control plots. Damage and development of all above-ground parts of the plants was recorded. Scoring was done on a percentage scale (100% action=all plants dead; 50% action=50% of the plants and green plant parts dead; 0% action=no discernible action=like control plot). The score figures of in each case 4 plots were averaged.

The growth stages of the different weed species are indicated according to the BBCH monograph "Growth stages of mono- and dicotyledonous plants", 2$^{nd}$ edition, 2001, ed. Uwe Meier, Federal Biological Research Centre for Agriculture and Forestry (Biologische Bundesanstalt für Land and Forstwirtschaft). The respective BBCH stages are indicated in brackets for the different weed species.

The dose rates of herbicidal ingredients used in each case are indicated for the respective active ingredient in brackets and refer to the amount of active ingredient per hectare (g/ha).

The following abbreviations for the active ingredient are used in the Tables below:
MSM: Mesosulfuron-methyl (A1-1) or Mesosulfuron-methyl-sodium (A1-2)
IMS: Iodosulfuron-methyl (B1-1) or Iodosulfuron-methyl-sodium (B1-2)
TCM: Thienecarbazone-methyl (C1-1)
PXD: Pinoxaden
PYX: Pyroxsulam
HALXF: Halauxifen The herbicidal effects observed for the herbicide (mixtures) are indicated in % Activity against the respective weed. The % Damage indicated refers to the maximum damage observed in the respective crop.

The results of the treatments are reflected in the Tables below, and the activity measured for the independent use of the active compounds (A+B)+(C) is stated in brackets. The treatments were carried out using Mesosulfuron-methyl (A1-1) or Mesosulfuron-methyl-sodium (A1-2) as component (A), and Iodosulfuron-methyl (B1-1) or Iodosulfuron-methyl-sodium (B1-2) as component (B). The results of the treatments in these cases were essentially identical.

TABLE 1A

Combination MSM + IMS + TCM
In the crop TRZDU: *Triticum aestivum* (durum wheat) the following weeds were treated (field trials).

| Weed (BBCH stage) | (MSM + IMS) (15 + 3 g/ha) | | TCM 7.5 g/ha | | (MSM + IMS) + TCM (15 + 3 g/ha) + 7.5 g/ha | |
|---|---|---|---|---|---|---|
| | % Activity | % Damage | % Activity | % Damage | % Activity | % Damage |
| PAPRH (15) | 90 | 0 | 70 | 0 | 99 (90 + 70) | 0 |
| PICEC (22) | 85 | 2 | 69 | 5 | 92 (85 + 69) | 5 |
| AVEST (23) | 63 | 0 | 33 | 0 | 100 (63 + 33) | 0 |
| LOLMU (23) | 72 | 0 | 43 | 0 | 98 (72 + 43) | 0 |
| LOLRI (29) | 80 | 5 | 52 | 5 | 100 (80 + 52) | 0 |

| Weeds treated (cf. Tables 1A and 1B) | BBCH stage |
|---|---|
| PAPRH: *Papaver rhoeas* | 15: 5 true leaves |
| PICEC: *Picris echioides* | 22: 2 tillers visible/2 side shoots visible |
| AVEST: *Avena sterilis* | 23: 3 tillers visible/3 side shoots visible |
| LOLMU: *Lolium multiflorum* | 23: 3 tillers visible/3 side shoots visible |
| LOLRI: *Lolium rigidum* | 29: 9 or more tillers visible/2 or more side shoots visible |

TABLE 1B

Combination MSM + IMS + TCM
In the crop TRZDU: *Triticum aestivum* (durum wheat) the following weeds were treated (field trials).
The same weed species were treated at the BBCH growth stages as in the case of Table 1A, however here a different ratio of MSM:IMS was used.

| Weed (BBCH stage) | (MSM + IMS) (9 + 9 g/ha) | | TCM 7.5 g/ha | | (MSM + IMS) + TCM (9 + 9 g/ha) + 7.5 g/ha | |
|---|---|---|---|---|---|---|
| | % Activity | % Damage | % Activity | % Damage | % Activity | % Damage |
| PAPRH (15) | 87 | 0 | 70 | 0 | 98 (87 + 70) | 0 |
| PICEC (22) | 97 | 5 | 69 | 5 | 99 (97 + 69) | 10 |

TABLE 1B-continued

Combination MSM + IMS + TCM
In the crop TRZDU: *Triticum aestivum* (durum wheat) the following weeds were treated (field trials). The same weed species were treated at the BBCH growth stages as in the case of Table 1A, however here a different ratio of MSM:IMS was used.

| Weed (BBCH stage) | (MSM + IMS) (9 + 9 g/ha) | | TCM 7.5 g/ha | | (MSM + IMS) + TCM (9 + 9 g/ha) + 7.5 g/ha | |
|---|---|---|---|---|---|---|
| | % Activity | % Damage | % Activity | % Damage | % Activity | % Damage |
| AVEST (23) | 63 | 0 | 33 | 0 | 70 (63 + 33) | 0 |
| LOLMU (23) | 65 | 0 | 43 | 0 | 88 (65 + 43) | 0 |
| LOLRI (29) | 63 | 5 | 52 | 5 | 74 (63 + 52) | 10 |

TABLE 2A

Combination MSM + IMS + TCM
In the crop TRZAW: *Triticum aestivum* (soft wheat) the following weeds were treated (field trials).

| Weed (BBCH stage) | (MSM + IMS) (15 + 3 g/ha) | | TCM 7.5 g/ha | | (MSM + IMS) + TCM (15 + 3 g/ha) + 7.5 g/ha | |
|---|---|---|---|---|---|---|
| | % Activity | % Damage | % Activity | % Damage | % Activity | % Damage |
| CENCY (19) | 25 | 1 | 38 | 0 | 92 (25 + 38) | 0 |
| GALAP (23) | 82 | 0 | 37 | 0 | 95 (82 + 37) | 0 |
| GERDI (29) | 43 | 1 | 63 | 0 | 98 (43 + 63) | 0 |
| LAMAM (32) | 75 | 10 | 68 | 1 | 99 (75 + 68) | 7 |
| LAMPU (61) | 78 | 10 | 70 | 1 | 96 (78 + 70) | 7 |
| MATIN (19) | 87 | 0 | 20 | 0 | 100 (87 + 20) | 0 |
| VERPE | 72 | 10 | 10 | 1 | 90 (72 + 10) | 7 |
| VIOAR (15) | 43 | 1 | 38 | 0 | 84 (43 + 38) | 0 |

| Weeds treated (cf. Tables 2A and 2B) | BBCH stage |
|---|---|
| CENCY: *Centaurea Cyanus* | 19: 9 or more true leaves |
| GALAP: *Galium aparine* | 23: 3 tillers visible/3 side shoots visible |
| GERDI: *Geranium dissectum* | 29: 9 or more tillers visible/2 or more side shoots visible |
| LAMAM: *Lamium amplexicaule* | 32: Stem (rossete) 20% of final length (diameter)/2 node |
| LAMPU: *Lamium purpureum* | 61: Beginning of flowering: 10% flowers open |
| MATIN: *Matricaria inodora* | 19: 9 or more true leaves |
| VERPE: *Veronica persica* | |
| VIOAR: *Viola arvensis* | 15: 5 true leaves |

TABLE 2B

Combination MSM + IMS + TCM
In the crop TRZAW: *Triticum aestivum* (soft wheat) the following weeds were treated (field trials). The same weed species were treated at the BBCH growth stages as in the case of Table 2A, however here a different ratio of MSM:IMS was used.

| Weed (BBCH stage) | (MSM + IMS) (9 + 9 g/ha) | | TCM 7.5 g/ha | | (MSM + IMS) + TCM (9 + 9 g/ha) + 7.5 g/ha | |
|---|---|---|---|---|---|---|
| | % Activity | % Damage | % Activity | % Damage | % Activity | % Damage |
| CENCY (19) | 37 | 2 | 38 | 0 | 93 (37 + 38) | 1 |
| GALAP (23) | 88 | 0 | 37 | 0 | 91 (88 + 37) | 0 |
| GERDI (29) | 91 | 2 | 63 | 0 | 98 (91 + 63) | 0 |
| LAMAM (32) | 88 | 3 | 68 | 1 | 93 (88 + 68) | 13 |
| LAMPU (61) | 88 | 3 | 70 | 1 | 95 (88 + 70) | 13 |
| MATIN (19) | 92 | 0 | 20 | 0 | 93 (92 + 20) | 0 |
| VERPE | 78 | 3 | 10 | 1 | 94 (78 + 10) | 13 |
| VIOAR (15) | 85 | 2 | 38 | 0 | 96 (85 + 38) | 1 |

TABLE 3

Combination MSM + IMS + PXD
In the crop TRZAW: *Triticum aestivum* (soft wheat) the following weeds were treated (field trials).

| Weed (BBCH stage) | (MSM + IMS) (15 + 3 g/ha) % Activity | (MSM + IMS) (15 + 3 g/ha) % Damage | PXD 60 g/ha % Activity | PXD 60 g/ha % Damage | (MSM + IMS) + PXD (15 + 3 g/ha) + 60 g/ha % Activity | (MSM + IMS) + PXD (15 + 3 g/ha) + 60 g/ha % Damage |
|---|---|---|---|---|---|---|
| CENCY (38) | 83 | 0 | 60 | 15 | 88 (83 + 60) | 15 |
| GERDI (19) | 68 | 0 | 30 | 4 | 78 (68 + 30) | 1 |
| VERHE (71) | 45 | 0 | 13 | 0 | 68 (45 + 13) | 9 |
| VERPE (31) | 33 | 0 | 0 | 0 | 53 (33 + 0) | 0 |
| BROST (25) | 89 | 0 | 0 | 0 | 98 (89 + 0) | 0 |

Weeds treated (cf. Table 3)  BBCH stage

CENCY: *Centaurea Cyanus*  38: Stem (rossete) 80% of final length (diameter)/8 node
GERDI: *Geranium dissectum*  19: 9 or more true leaves
VERHE: *Veronica hederifolia*  71: 10% fruits have reached final size or 10% final size
VERPE: *Veronica persica*  31: Stem (rossete) 10% of final length (diameter)/1 node
BROST: *Bromus sterilis*  25: 5 tillers visible/5 side shoots visible

TABLE 4

Combination MSM + IMS + PYX

| Weed (BBCH stage) | (MSM + IMS) (7.5 + 1.5 g/ha) % Activity | PYX 17 g/ha % Activity | (MSM + IMS) + PYX (7.5 + 1.5 g/ha) + 17 g/ha % Activity |
|---|---|---|---|
| LOLRI (10) | 35 | 20 | 73 (35 + 20) |

Weed treated (cf. Table 4): LOLRI: *Lolium rigidum* at BBCH stage 10 (1 true leaf)

TABLE 5

Combination MSM + IMS + HALXF
In the crop TRZAW: *Triticum aestivum* (soft wheat) the following weeds were treated.

| Weed | (MSM + IMS) (9 + 1.8 g/ha) % Activity | (MSM + IMS) (9 + 1.8 g/ha) % Damage | HALXF 276.5 g/ha % Activity | HALXF 276.5 g/ha % Damage | (MSM + IMS) + HALXF (9 + 1.8 g/ha) + 276.5 g/ha % Activity | (MSM + IMS) + HALXF (9 + 1.8 g/ha) + 276.5 g/ha % Damage |
|---|---|---|---|---|---|---|
| CENCY | 40 | 0 | 45 | 0 | 85 (40 + 45) | 5 |
| FUMOF | 93 | 0 | 85 | 0 | 99 (93 + 85) | 5 |
| GALAP | 88 | 0 | 73 | 0 | 98 (88 + 73) | 5 |
| PAPRH | 83 | 0 | 75 | 0 | 95 (83 + 75) | 5 |

Weeds treated (cf. Table 5):

CENCY: *Centaurea Cyanus*
FUMOF: *Fumaria officinalis*
GALAP: *Gallium aparine*
PAPRH: *Papaver rhoeas*

The invention claimed is:

1. An herbicide composition comprising components (A), (B) and (C), wherein
   (A) denotes mesosulfuron-methyl (A1-1) and/or mesosulfuron-methyl sodium (A1-2),
   (B) denotes iodosulfuron-methyl (B1-1) and/or iodosulfuron-methyl sodium (B1-2),
   (C) denotes at least one compound selected from the group consisting of
      (C-1) thiencarbazone-methyl or a salt thereof;
      (C-4) pinoxaden or a salt thereof
   wherein the weight ratio of the components A and B to one another is 5:1 to 1:1,
   wherein the weight ratio of the two components (A+B) and C to each other is 3:1 to 1:1, wherein C is (C-1) thiencarbazone-methy or a salt thereofl,
   wherein the weight ratio of the two components (A+B) and C to each other is 1:1 to 1:4, wherein C is (C-4) pinoxaden or a salt thereof,
   and wherein (A), (B), and (C) are the only herbicides in the composition.

2. The herbicide composition as claimed in claim 1 which additionally comprises one or more further components selected from the group consisting of agrochemically active compounds of a different type, formulation auxiliaries and additives customary in crop protection.

3. The herbicide composition as claimed in claim 1 which additionally comprises one or more safeners.

4. The herbicide composition as claimed in claim 3, wherein the safener is, mefenpyr-diethyl (S1-1).

5. The herbicide composition as claimed in claim 1, which additionally comprises one or more fatty alcohol polyglycol esters and/or one or more vegetable oils.

6. The herbicide composition according to claim 1, wherein component (C) is (C-1) thiencarbazone-methyl and/or a salt thereof.

7. The herbicide composition according to claim 1, wherein component (C) is (C-4) pinoxaden and/or a salt thereof.

8. The herbicide composition according to claim 1,
wherein C is (C-1) thiencarbazone-methyl or a salt thereof, and
wherein the weight ratio of the two components (A+B) and C to each other is 5:2 to 3:2.

9. The herbicide composition according to claim 1,
wherein C is (C-4) pinoxaden or a salt thereof, and
wherein the weight ratio of the two components (A+B) and C to each other is 1:2 to 1:4.

10. A method for controlling undesired plant growth which comprises applying herbicides (A), (B) and (C) onto a plant, a part of plants, one or more plant seeds and/or an area where plants grow,
wherein
(A) denotes mesosulfuron-methyl (A1-1) and/or mesosulfuron-methyl sodium (A1-2),
(B) denotes iodosulfuron-methyl (B1-1) and/or iodosulfuron-methyl sodium (B1-2),
(C) denotes at least one compound selected from the group consisting of
(C-1) thiencarbazone-methyl or a salt thereof;
(C-4) pinoxaden or a salt thereof;
wherein the weight ratio of the components A and B to one another is 5:1 to 1:1,
wherein the weight ratio of the two components (A+B) and C to each other is 3:1 to 1:1 wherein C is (C-1) thiencarbazone-methyl or a salt thereof,
wherein the weight ratio of the two components (A+B) and C to each other is 1:1 to 1:4, wherein C is (C-4) pinoxaden or a salt thereof,
wherein components (A), (B), and (C) are present in synergistic effective amounts,
and wherein (A), (B), and (C) are the only herbicides in the method.

11. The method as claimed in claim 10 comprising the selective control of harmful plants in one or more plant crops.

12. The method as claimed in claim 11 comprising the control of harmful plants in crops of monocotyledonous plants.

13. The method as claimed in claim 11 in which the plant crops are genetically modified or have been obtained by mutation/selection.

14. The method according to claim 10, wherein the herbicides (A), (B), and (C) are applied together.

15. The method according to claim 10, wherein component (C) is (C-1) thiencarbazone-methyl and/or a salt thereof.

16. The method according to claim 10, wherein component (C) is (C-4) pinoxaden and/or a salt thereof.

17. The method according to claim 10,
wherein C is (C-1) thiencarbazone-methyl or a salt thereof, and
wherein the weight ratio of the two components (A+B) and C to each other is 5:2 to 3:2.

18. The method according to claim 10,
wherein C is (C-4) pinoxaden or a salt thereof, and
wherein the weight ratio of the two components (A+B) and C to each other is 1:2 to 1:4.

* * * * *